(12) United States Patent
Tennican

(10) Patent No.: US 10,894,153 B2
(45) Date of Patent: Jan. 19, 2021

(54) PORT AND SURFACE CLEANING DEVICES AND TECHNIQUES

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

(*) Notice: Subject to any disclaimer, the term of this patent is extended or adjusted under 35 U.S.C. 154(b) by 140 days.

(21) Appl. No.: 16/298,656

(22) Filed: Mar. 11, 2019

(65) Prior Publication Data
US 2019/0201680 A1    Jul. 4, 2019

Related U.S. Application Data

(62) Division of application No. 13/688,044, filed on Nov. 28, 2012, now Pat. No. 10,238,856.
(Continued)

(51) Int. Cl.
| A61M 39/16 | (2006.01) |
| A01N 59/00 | (2006.01) |
| A61K 33/40 | (2006.01) |
| A61M 11/08 | (2006.01) |
| A61M 15/08 | (2006.01) |

(Continued)

(52) U.S. Cl.
CPC ........... *A61M 39/162* (2013.01); *A01N 59/00* (2013.01); *A61K 33/40* (2013.01); *A61M 11/08* (2013.01); *A61M 15/08* (2013.01); *A61M 25/002* (2013.01); *A61M 25/0017* (2013.01); *A61M 39/20* (2013.01); *A61K 9/0014* (2013.01); *A61K 47/183* (2013.01); *A61M 35/00* (2013.01); *A61M 39/165* (2013.01); *A61M 2025/0019* (2013.01); *A61M 2205/583* (2013.01);
(Continued)

(58) Field of Classification Search
CPC ............ A61M 25/0017; A61M 39/162; A61M 39/20; A61M 39/165; A61M 25/002; A61M 2025/0018; A61M 2025/0019; A61B 1/122; A61B 2050/3005; A61B 50/39; A61L 2/235; A61L 2/26; A61L 2202/181; A61L 2202/23; A61L 2202/24
USPC ........ 604/286, 369, 370; 206/531, 532, 571, 206/364
See application file for complete search history.

(56) References Cited

U.S. PATENT DOCUMENTS

| 3,648,704 A | 3/1972 | Jackson |
| 3,967,728 A | 7/1976 | Gordon et al. |

(Continued)

FOREIGN PATENT DOCUMENTS

| CN | 1389186 A | 1/2003 |
| CN | 1717261 | 1/2006 |

(Continued)

OTHER PUBLICATIONS

The Canadian Office Action dated Jul. 12, 2019 for Canadian patent application No. 2,856,534, a counterpart foreign application of U.S. Appl. No. 13/688,044, 5 pages.

(Continued)

*Primary Examiner* — Deanna K Hall
(74) *Attorney, Agent, or Firm* — Lee & Hayes PC

(57) ABSTRACT

This disclosure describes example antimicrobial compositions that may be used in combination with IV port cleansing caps, protective caps, or both. According to another implementations, the disclosure describes various cap devices that may be used in combination with the antimicrobial composition to cleanse, sanitized, and/or disinfected a surface.

20 Claims, 8 Drawing Sheets

Related U.S. Application Data

(60) Provisional application No. 61/564,206, filed on Nov. 28, 2011.

(51) Int. Cl.
  *A61M 39/20* (2006.01)
  *A61M 25/00* (2006.01)
  *A61K 9/00* (2006.01)
  *A61K 47/18* (2017.01)
  *A61M 35/00* (2006.01)

(52) U.S. Cl.
  CPC .. *A61M 2209/06* (2013.01); *F04C 2270/0421* (2013.01); *Y10S 604/905* (2013.01)

(56) References Cited

U.S. PATENT DOCUMENTS

| | | | |
|---|---|---|---|
| 4,334,551 | A | 6/1982 | Pfister |
| 4,360,020 | A | 11/1982 | Hitchcock, Jr. et al. |
| 4,811,847 | A | 3/1989 | Reif et al. |
| 5,048,684 | A | 9/1991 | Scott |
| 5,226,530 | A | 7/1993 | Golden |
| 6,090,075 | A | 7/2000 | House |
| 7,780,794 | B2 | 8/2010 | Rogers et al. |
| 7,981,090 | B2 | 7/2011 | Plishka et al. |
| 8,336,152 | B2 | 12/2012 | Vaillancourt et al. |
| 2001/0001443 | A1 | 5/2001 | Kayerod et al. |
| 2001/0052664 | A1 | 12/2001 | Saitoh |
| 2003/0018322 | A1 | 1/2003 | Tanghoj et al. |
| 2005/0265773 | A1 | 12/2005 | De Laforcade |
| 2006/0142737 | A1 | 6/2006 | Tanghoj |
| 2007/0161949 | A1 | 7/2007 | Knox et al. |
| 2007/0213645 | A1 | 9/2007 | Zumeris et al. |
| 2007/0282280 | A1 | 12/2007 | Tennican |
| 2008/0019889 | A1 | 1/2008 | Rogers et al. |
| 2008/0033371 | A1 | 2/2008 | Updegraff et al. |
| 2008/0038167 | A1 | 2/2008 | Lynn |
| 2008/0132880 | A1 | 6/2008 | Buchman |
| 2009/0024111 | A1 | 1/2009 | Borodulin et al. |
| 2009/0028750 | A1 | 1/2009 | Ryan |
| 2009/0299334 | A1 | 12/2009 | Nishtala et al. |
| 2009/0324508 | A1 | 12/2009 | Bobbert |
| 2010/0000040 | A1 | 1/2010 | Shaw et al. |
| 2010/0242993 | A1 | 9/2010 | Hoang et al. |
| 2011/0030726 | A1 | 2/2011 | Vaillancourt et al. |
| 2011/0052664 | A1 | 3/2011 | Tennican et al. |
| 2011/0064512 | A1 | 3/2011 | Shaw et al. |
| 2011/0171280 | A1 | 7/2011 | Toreki et al. |
| 2011/0201692 | A1 | 8/2011 | Raad |
| 2011/0301553 | A1 | 12/2011 | Goral et al. |
| 2013/0030414 | A1 | 1/2013 | Gardner et al. |

FOREIGN PATENT DOCUMENTS

| | | |
|---|---|---|
| CN | 1806746 | 7/2006 |
| CN | 101306221 | 11/2008 |
| CN | 101405042 | 4/2009 |
| CN | 101505815 | 8/2009 |
| CN | 101618384 | 1/2010 |
| CN | 101878050 | 11/2010 |
| DE | 29608617 | 8/1996 |
| JP | H03-48830 | 9/1960 |
| JP | H05212091 | 8/1993 |
| JP | H08215311 | 8/1996 |
| JP | 2000153876 | 6/2000 |
| JP | 2003261177 | 9/2003 |
| JP | 2007051111 A | 3/2007 |
| JP | 2007504927 A | 3/2007 |
| JP | 2007089599 | 4/2007 |
| JP | 2000056273 | 3/2009 |
| JP | 2009056273 | 3/2009 |
| JP | 2009537250 | 10/2009 |
| JP | 2013503713 | 2/2013 |
| JP | 2013518056 | 5/2013 |
| KR | 20090003267 | 1/2009 |
| KR | 20110043640 | 4/2011 |
| WO | WO2000025846 | 5/2000 |
| WO | WO0165939 | 9/2001 |
| WO | WO2003064279 | 8/2003 |
| WO | WO2006071781 | 7/2006 |
| WO | WO2007137056 | 11/2007 |
| WO | WO2009076718 | 6/2009 |
| WO | WO2010002757 | 1/2010 |
| WO | WO2011022601 | 2/2011 |
| WO | WO2011028965 | 3/2011 |
| WO | WO2011053924 | 5/2011 |
| WO | WO2011091322 | 7/2011 |
| WO | WO2011109393 | 9/2011 |
| WO | WO2012067778 | 5/2012 |

OTHER PUBLICATIONS

The Australian Office Action dated Oct. 14, 2016 for Australian Patent Application No. 2012346030, a counterpart foreign application of U.S. Appl. No. 13/688,073, 4 pages.

The Austrlian Office Action dated Oct. 25, 2016 for Australian Patent Application No. 2012346036, a counterpart foreign application of U.S. Appl. No. 13/688,044, 3 pages.

The Australian Office Action dated Oct. 7, 2015 for Australian patent application No. 2012346043, a counterpart foreign application of U.S. Appl. No. 13/688,044, 3 pages.

The Australian Office Action dated Nov. 26, 2015 for Australian patent application No. 2012346043, a counterpart foreign application of U.S. Appl. No. 13/688,044, 3 pages.

The Australian Office Action dated Mar. 2, 2017 for Australian Patent Application No. 2012346030, a counterpart foreign application of U.S. Appl. No. 13/688,073, 4 pages.

The Australian Office Action dated Jul. 11, 2016 for Australian patent application No. 2012346036, a counterpart foreign application of U.S. Appl. No. 13/688,044, 4 pages.

The Australian Office Action dated Jul. 19, 2016 for Australian Patent Application No. 2012346043, a counterpart foreign application of U.S. Appl. No. 13/688,044, 3 pages.

The Australian Office Action dated Jul. 31, 2017 for Australian Patent Application No. 2012346030, a counterpart foreign application of U.S. Appl. No. 13/688,073, 8 pages.

The Australian Office Action dated Sep. 28, 2017 for Australian Patent Application No. 2012346030, a counterpart foreign application of U.S. Appl. No. 13/688,073, 6 pages.

Translated Brazilian Pre-Examination Opinion dated Jan. 15, 2019 for Brazilian Patent Application No. BR1120140127077, a counterpart of U.S. Appl. No. 13/688,044, 2 pages.

The Canadian Office Action dated Oct. 12, 2018 for Canadian patent application No. 2,856,534, a counterpart foreign application of U.S. Appl. No. 13/688,044, 6 pages.

The Canadian Office Action dated Dec. 11, 2018 for Canadian patent application No. 2856535, a counterpart foreign application of U.S. Appl. No. 13/688,044, 4 pages.

The Canadian Office Action dated Sep. 19, 2018 for Canadian patent application No. 2856539, a counterpart foreign application of U.S. Appl. No. 13/688,044, 6 pages.

Translated Chinese Office Action dated Mar. 16, 2018 for Chinese Patent Application No. 201280058307.6, a counterpart foreign application of U.S. Appl. No. 13/688,073, 11 pages.

Translated Chinese Office Action dated Jan. 23, 2017 for Chinese Patent Application No. 201280058307.6, a counterpart foreign application of U.S. Appl. No. 13/688,044, 15 pages.

Translated Chinese Office Action dated Oct. 25, 2016 for Chinese Patent Application No. 201280058237.4, a counterpart foreign application of U.S. Appl. No. 13/688,044, 17 pages.

Translated Chinese Office Action dated Nov. 13, 2015 for Chinese patent application No. 201280058237.4, a counterpart foreign application of U.S. Appl. No. 13/688,044, 18 pages.

Translated Chinese Office Action dated Nov. 7, 2017 for Chinese patent application No. 201280058307.6, a counterpart foreign application of U.S. Appl. No. 13/688,073, 11 pages.

(56) References Cited

OTHER PUBLICATIONS

Translated Chinese Office Action dated Feb. 14, 2016 for Chinese patent application No. 201280058307.6, a counterpart foreign application of U.S. Appl. No. 13/688,044, 16 pages.
Translated Chinese Office Action dated Feb. 6, 2016 for Chinese patent application No. 201280058316.5, a counterpart foreign application of U.S. Appl. No. 13/688,044, 29 pages.
Translated Chinese Office Action dated Mar. 31, 2015 for Chinese patent application No. 201280058237.4, a counterpart foreign application of U.S. Appl. No. 13/688,044, 20 pages.
Translated Chinese Office Action dated Apr. 28, 2017 for Chinese patent application No. 201280058316.5, a counterpart foreign application of U.S. Appl. No. 13/688,044, 20 pages.
Translated Chinese Office Action dated May 11, 2016 for Chinese patent application No. 201280058316.5, a counterpart foreign applicaton of U.S. Appl. No. 13/688,044, 28 pages.
Translated Chinese Office Action dated May 5, 2016 for Chinese Patent Application No. 201280058237.4, a counterpart foreign application of U.S. Appl. No. 13/688,044, 18 pages.
Translated Chinese Office Action dated Jul. 4, 2016 for Chinese patent application No. 201280058307.6, a counterpart foreign application of U.S. Appl. No. 13/688,044, 15 pages.
Translated Chinese Office Action dated Aug. 18, 2017 for Chinese patent application No. 201280058316.5, a counterpart foreign application of U.S. Appl. No. 13/688,044.
Translated Chinese Office Action dated Aug. 28, 2015 for Chinese patent application No. 201280058307.6, a counterpart foreign application of U.S. Appl. No. 13/688,044, 16 pages.
Translated Chinese Office Action dated Sep. 14, 2015 for Chinese patent application No. 201280058316.5, a counterpart foreign application of U.S. Appl. No. 13/688,044, 22 pages.
Translated Chinese Office Action dated Sep. 28, 2016 for Chinese patent application No. 201280058316.5, a counterpart foreign application of U.S. Appl. No. 13/688,044, 24 pages.
The European Office Action dated Jun. 21, 2018 for European patent application No. 12853916.0, a counterpart foreign application of U.S. Appl. No. 13/688,044, 5 pages.
The European Office Action dated Sep. 25, 2015 for European patent application No. 12853916.0, a counterpart foreign application of U.S. Appl. No. 13/688,044, 3 pages.
The European Office Action dated Sep. 25, 2015 for European patent application No. 12852866.8, a counterpart foreign application of U.S. Appl. No. 13/688,078, 3 pages.
The European Office Action dated Sep. 25, 2015 for European patent application No. 12852889.0, a counterpart foreign application of U.S. Appl. No. 13/688,073, 3 pages.
The European Office Action dated Sep. 8, 2016 for European Patent Application No. 12852866.8, a counterpart foreign application of U.S. Appl. No. 13/688,078, 4 pages.
The European Office Action dated Oct. 25, 2016 for European Patent Application No. 12852889.0, a counterpart foreign application of U.S. Appl. No. 13/688,073, 4 pages.
The Extended European Search Report dated Jan. 14, 2016 for European Patent Application No. 12852889.0, 9 pages.
The Extended European Search Report dated Jan. 7, 2016 for European Patent Application No. 12852866.8, 8 pages.
The Extended European Search Report dated Jan. 7, 2016 for European patent application No. 12853916.0, 9 pages.
Hooton et al, "Diagnosis, Prevention, and Treatment of Catheter-Associated Urinary Tract Infection in Adults: 2009 Intl Clinical Practice Guidelines from the Infectious Disease Society of America", Mar. 2010, Urinary Catheter Guidelines, Clinical Infectious Diseases, vol. 50, 39 pgs.
Translated Japanese Office Action dated Jan. 24, 2017 for Japanese Patent Application No. 2014-543631, a counterpart foreign application of U.S. Appl. No. 13/688,078, 4 pages.
Translated Japanese Office Action dated Dec. 25, 2017 for Japanese Patent Application No. 2014-543627, a counterpart foreign application of U.S. Appl. No. 13/688,073, 5 pages.

Translated Japanese Office Action dated Jun. 13, 2017 for Japanese Patent Application No. 2014-543627, a counterpart foreign application of U.S. Appl. No. 13/688,073, 10 pages.
Translated Japanese Office Action dated Jun. 27, 2017 for Japanese Patent Application No. 2014-543628, a counterpart foreign application of U.S. Appl. No. 13/688,044, 9 pages.
Translated Japanese Office Action dated Sep. 20, 2016 for Japanese Patent Application No. 2014-543628, a counterpart foreign application of U.S. Appl. No. 13/688,044, 13 pages.
Translated Japanese Office Action dated Sep. 20, 2016 for Japanese Patent Application No. 2014-543627, a counterpart foreign application of U.S. Appl. No. 13/688,073, 13 pages.
Translated Japanese Office Action dated Nov. 27, 2018 for Japanese Patent Application No. 2014-543627, a counterpart foreign application of U.S. Appl. No. 13/688,073.
Translated Japanese Office Action dated Oct. 4, 2016 for Japanese Patent Application No. 2014-543631, a counterpart foreign application of U.S. Appl. No. 13/688,078, 13 pages.
Translated Japanese Office Action dated Dec. 18, 2018 for Japanese Patent Application No. 2014-543628, a counterpart of U.S. Appl. No. 13/688,044, 14 pages.
Translated Japanese Office Action dated Dec. 19, 2017 for Japanse patent application No. 2014-543628, a counterpart foreign application of U.S. Appl. No. 13/688,044, 4 pages.
The Canadian Office Action dated May 7, 2019 for Canadian patent application No. 2856539, a counterpart foreign application of U.S. Appl. No. 13/688,044, 3 pages.
The Korean Office Action dated May 22, 2019 for Korean Patent Application No. 10-2014-7014438, a counterpart of U.S. Pat. No. 10,238,856, 12 pages.
The Mexican Office Action dated Apr. 9, 2019 for Mexican Patent Application No. MX/a/2014/006412, a counterpart of U.S. Pat. No. 10,238,856, 9 pages.
Translated Korean Office Action dated Feb. 18, 2019 for Korean Patent Application No. 10-2014-7014331, a counter part of U.S. Appl. No. 13/688,044, 8 pages.
Translated Mexican Office Action dated Jan. 29, 2019 for Mexican patent application No. MX/a/2014/006414, a counterpart foreign application of U.S. Appl. No. 13/688,073, 7 pages.
Translated Mexican Office Action dated Oct. 9, 2017 for Mexican patent application No. MX/a/2014/006413, a counterpart foreign application of U.S. Appl. No. 13/688,044, 4 pages.
The Mexican Office Action dated Nov. 27, 2018 for Mexican Patent Application No. MX/a/2014/006413, a counterpart of U.S. Appl. No. 13/688,044, 3 pages.
Translated Mexican Office Action dated Apr. 10, 2018 for Mexican patent application No. MX/a/2014/006413, a counterpart foreign application of U.S. Appl. No. 13/688,044.
Translated Mexican Office Action dated Apr. 20, 2018 for Mexican patent application No. MX/a/2014/006414, a counterpart foreign application of U.S. Appl. No. 13/688,073.
Office action for U.S. Appl. No. 13/688,044, dated Jan. 12, 2017, Tennican, "Port and Surface Cleaning Devices and Techniques", 8 pages.
Final Office Action for U.S. Appl. No. 13/688,073, dated Jan. 15, 2015, Patrick O. Tennican, "Catheter Devices and Techniques", 18 pages.
Office Action for U.S. Appl. No. 13/688,073, dated Oct. 25, 2013, Patrick O. Tennican, "Catheter Devices and Techniques", 11 pages.
Final Office Action for U.S. Appl. No. 13/688,044, dated Oct. 30, 2015, Patrick O. Tennican, "Port and Surface Cleaning Devices and Techniques", 10 pages.
Office action for U.S. Appl. No. 13/688,078, dated Nov. 8, 2017, Tennican, "Antimicrobial Composition Including a Residual Barrier Film", 11 pages.
Office action for U.S. Appl. No. 13/688,044, dated Dec. 20, 2017, Tennican, "Port and Surface Cleaning Devices and Techniques", 12 pages.
Office action for U.S. Appl. No. 13/688,078, dated Feb. 28, 2017, Tennican, "Antimicrobial Composition Including a Residual Barrier Film", 9 pages.

(56) References Cited

OTHER PUBLICATIONS

Office action for U.S. Appl. No. 13/688,044, dated Apr. 1, 2016, Tennican, "Port and Surface Cleaning Devices and Techniques", 10 pages.

Final Office Action for U.S. Appl. No. 13/688,073, dated Apr. 18, 2014, Patrick O. Tennican, "Catheter Devices and Techniques", 13 pages.

Non-Final Office Action for U.S. Appl. No. 13/688,073, dated May 23, 2013, Patrick O. Tennican, "Catheter Devices and Techniques ", 13 pages.

Office Action for U.S. Appl. No. 13/688,044, dated May 28, 2015, Patrick O. Tennican, "Port and Surface Cleaning Devices and Techniques", 9 pages.

Office action for U.S. Appl. No. 13/688,044, dated Jun. 21, 2017, Tennican, "Port and Surface Cleaning Devices and Techniques", 9 pages.

Office action for U.S. Appl. No. 13/688,078, dated Jun. 29, 2017, Tennican, "Antimicrobial Composition Including a Residual Barrier Film", 13 pages.

Office action for U.S. Appl. No. 13/688,078, dated Jun. 3, 2016, Tennican, "Antimicrobial Composition ncluding a Residual Barrier Film", 8 pages.

Office Action for U.S. Appl. No. 13/688,078, dated Aug. 13, 2015, Patrick O. Tennican, "Antimicrobial Composition Including a Residual Barrier Film", 14 pages.

Office action for U.S. Appl. No. 13/688,044, dated Aug. 19, 2016, Tennican, "Port and Surface Cleaning Devices and Techniques", 9 pages.

Office Action for U.S. Appl. No. 13/688,073, dated Sep. 12, 2014, Patrick O. Tennican, "Catheter Devices and Techniques", 12 pages.

Office action for U.S. Appl. No. 13/688,078, dated Sep. 9, 2016, Tennican, "Antimicrobial Composition Including a Residual Barrier Film", 9 pages.

The PCT Search Report dated Feb. 26, 2013 for PCT application No. PCT/US12/66894, 11 pages.

The PCT Search Report dated Mar. 4, 2013 for PCT application No. PCT/US12/66880, 12 pages.

The PCT Search Report dated Apr. 1, 2013 for PCT application No. PCT/US12/66886, 13 pages.

The Korean Office Action dated Mar. 25, 2019 for Korean Patent Application No. 10-2014-7014439, a counterpart of U.S. Pat. No. 10,238,856, 7 pages.

The Brazilian Office Action dated Nov. 19, 2019 for Brazilian Patent Application No. BR112014012802-2, a counterpart of U.S. Pat. No. 10,238,856, 7 pages.

The Brazilian Office Action dated Nov. 19, 2019 for Brazilian Patent Application No. BR112014012689-5, a counterpart of U.S. Pat. No. 10,238,856, 7 pages.

The Indian Office Action dated Dec. 12, 2019 for Indian Patent Application No. 4271/DELNP/2014, a counterpart foreign application of the U.S. Appl. No. 13/688,044, 6 pages.

The Korean Office Action dated Nov. 22, 2019 for Korean Patent Application No. 10-2014-7014438, a counterpart of U.S. Pat. No. 10,238,856, 11 pages.

The Korean Office Action dated Sep. 24, 2019 for Korean Patent Application No. 10-2014-7014439, a counterpart of U.S. Appl. No. 13/688,044, 10 pages.

The Mexican Office Action dated Oct. 1, 2019 for Mexican Patent Application No. MX/a/2014/006412, a counterpart foreign application of the U.S. Appl. No. 13/688,078, 7 pages.

The Indian Office Action dated Mar. 2, 2020, for Indian Patent Application No. 4272/DELNP/2014, a counterpart foreign application of the U.S. Pat. No. 10,238,856, 7 pages.

The Canadian Office Action dated Aug. 29, 2019 for Canadian Patent Application No. 2,856,535, a counterpart of U.S. Pat. No. 10,238,856, 4 pages.

The Korean Office Action dated Aug. 28, 2019 for Korean Patent Application No. 10-2014-7014331, a counter part of U.S. Appl. No. 13/688,044, 6 pages.

The Chinese Office Action dated Dec. 26, 2019 for Chinese Patent Application No. 201711159884.5, a counterpart foreign application of the U.S. Pat. No. 10,238,856, 22 pages.

The Indian Office Action dated Feb. 18, 2020, for Indian Patent Application No. 4270/DELNP/2014, a counterpart foreign application of the U.S. Pat. No. 10,238,856, 7 pages.

PORT AND SURFACE CLEANING DEVICES AND TECHNIQUES

CROSS REFERENCE TO RELATED APPLICATION

This application is a divisional of and claims priority to U.S. patent application Ser. No. 13/688,044, filed on Nov. 28, 2012, now U.S. Pat. No. 10,238,856, issued Mar. 26, 2019, which claims the benefit of U.S. Provisional Patent Application No. 61/564,206 filed on Nov. 28, 2011, entitled "Medical Devices and Techniques for Antiseptic, Immunomodulatory and Antineoplastic Therapies," each of which is hereby incorporated by reference in its entirety.

BACKGROUND

Infection remains a real problem in the medical industry today. Infections are often caused by contamination of intravascular (IV) lines (e.g., intravenous, intra-arterial, etc.), contamination of an injection site or blood draw site (e.g., from a vein, artery, or capillary), urinary catheters, wound sites, incision sites, and numerous other sources of infection in healthcare facilities. For example, in United States hospitals alone, central venous catheters cause an estimated 250,000 blood stream infections per year, which result substantial costs, both in terms of financial resources consumed and in patient morbidity. O'Grady, M D, et al., *Guidelines for the Prevention of Intravascular Catheter-Related Infections*, 2011, Center for Disease Control, Department of Health and Human Services. These numbers do not include infections caused contamination of injection sites, blood draw sites, non-venous catheters, or any of the other numerous sources of contamination in healthcare facilities. Infection is even more of a problem in developing nations, where syringes, IV lines, and other equipment routinely are used and re-used for multiple different patients.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

This application describes approaches to reducing and/or preventing infections. In one aspect, the application describes example antimicrobial compositions that may be used alone or in combination with one or more medical devices to clean and/or disinfect intravascular (IV) line ports, other IV components (e.g., syringes, lumens, valves, etc.), injection sites, blood draw sites (e.g., from a vein, artery, or capillary), wound sites, incision sites, peritoneal dialysis sites, bladder or nephrostomy sites, other drainage sites, or any other site that is susceptible to infection.

Example Port Protection and Cleaning Devices

FIGS. 1A-5C illustrate details of several example port cleaning and protecting caps. Each of the caps may be made of materials such as, but not limited to, polyethylene, polypropylene, copolymer materials and/or mixtures thereof. The caps may also comprise a material or agent that is UV protective to preserve the integrity of hydrogen peroxide during storage, shipping, etc. The caps themselves may additionally or alternatively be housed in a packaging that contains UV protective materials to inhibit breakdown of the hydrogen peroxide.

Figures 1A, 1B:
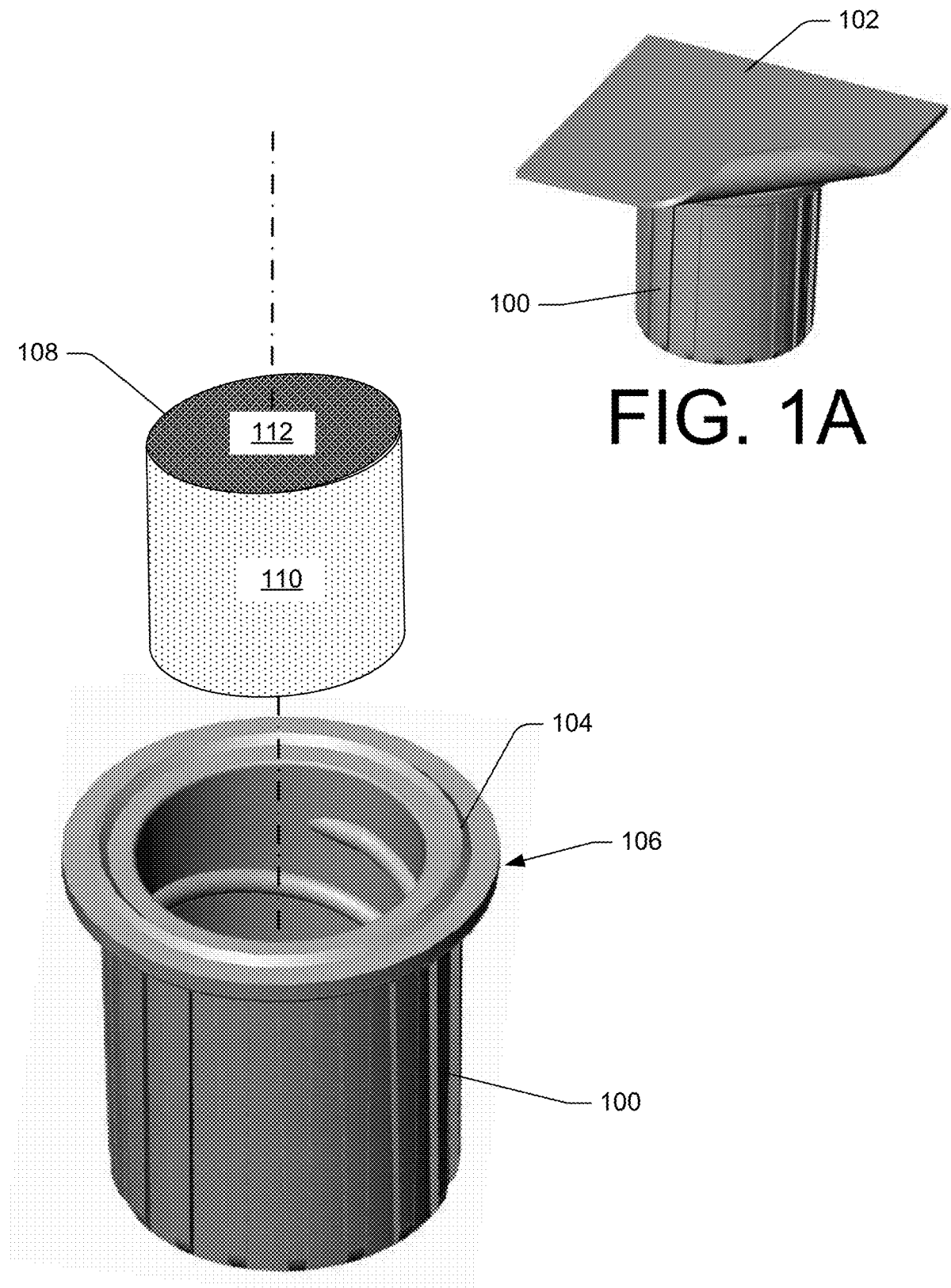
FIGS. 1A and 1B illustrate an example port protective cap.

FIGS. 1A and 1B illustrate an example of an IV port protective cap 100 designed to thread onto a threaded port, such as a female Leur® connector, to provide a physical barrier against recontamination. As shown in FIG. 1A, the protective cap 100 is hermetically sealed by a protective cover 102. The protective cap 100 may be removably fused or bonded to the protective cap 100 by sonic welding, microwave welding, thermal fusion, or other bonding techniques. The protective cover 102 may be made of a same or different material than the protective cap 100. To facilitate the sealing of the protective cover 102 to the protective cap 100, as shown in FIG. 1B, the protective cap includes an energy director 104 disposed on a top surface of a rim 106 or flange surrounding an opening of the protective cap 100. The energy director 104 comprises a raised ridge or rib of material having a small cross section relative to the rim 106 of the protective cap 100. The small cross section of the energy director 104 allows the energy director to melt more quickly and to fuse with the protective cover 102 with less energy than that required to melt the entire rim 106 of the protective cap 100. The energy director 104 also allows the protective cover 102 to fuse to the protective cap 100 over a relatively thin region, thereby making the protective cover 102 easier to remove from the protective cap 100 than if it were fused over the entire area of the rim 106 of the protective cap 100.

The rim 106 is designed as a "no touch rim," which extends radially from the perimeter of the main body of the protective cap 100, thereby minimizing a likelihood that a user's fingers will come in contact with the internal surfaces of the protective cap during use. In the illustrated embodiment, the energy director 104 is disposed radially outward of an opening of the protective cap, but inward of an outer edge of the rim 106. This ensures that the portion of the rim 106 inside the energy director 104 remains sterile prior to use. The no touch rim 106 increases the likelihood that the portion of the rim 106 inside the energy director 104 remains sterile even during use. In other embodiments, the energy director may be disposed anywhere on the rim 106 (e.g., centrally as shown, at an inner perimeter of the rim proximate the opening, or at an outer perimeter of the rim).

As shown in FIG. 1B, the protective cap 100 also includes an applicator material 108 (shown in exploded view in this figure for clarity). In the illustrated example, the applicator material comprises a cylindrical foam material having an open cell region 110 around the circumference of the sides of the cylinder and a closed cell region 112 on one or both axial ends of the cylinder. The open cell region 110 allows the applicator material 108 to absorb and carry an antimicrobial composition, such as those described below. The closed cell region 112 serves to at least partially cover and seal an end of an IV port to prevent the IV port from leaking and to prevent substantial amounts of an antimicrobial composition from entering the IV port. Both the open cell region 110 and the closed cell region 112 may have a certain amount of texture or roughness to scrub the IV port. In some embodiments, the applicator material may comprise polyurethane, silicon, silicon rubber, polyethylene, polypropylene, thermoplastic elastomer, or the like and mixtures thereof Also, while applicator material 108 is illustrated as being a generally cylindrical body, in other embodiments, the applicator material may take on other shapes and/or sizes. Further, the applicator material 108 may include different surface treatments (e.g., siping, slitting, etc.), surface finishes (e.g., macro-, micro-, or nano-structures, etc.), and/or contours (e.g., rounded, ribbed, protrusions, fingers, etc.).

Figure 2A:
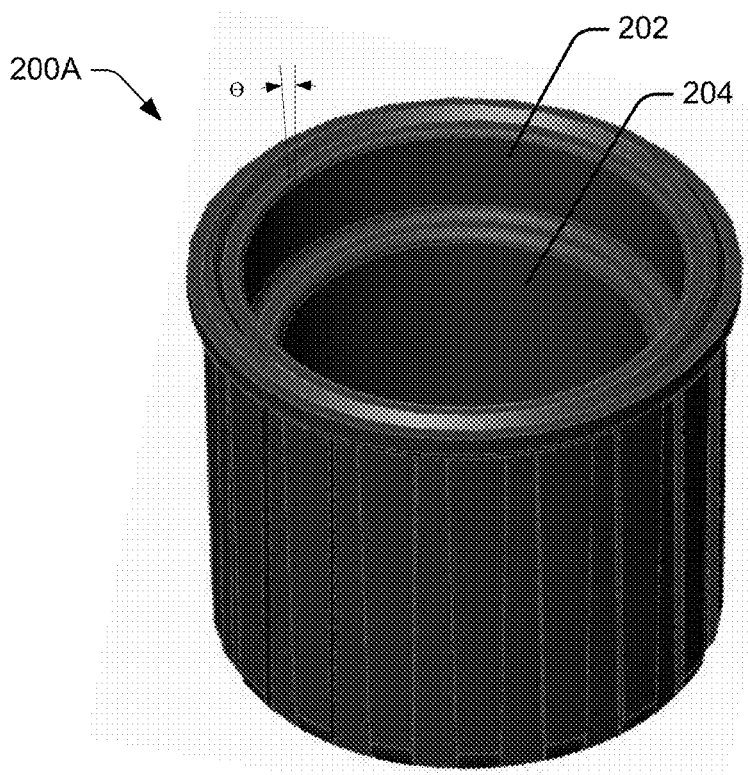
FIGS. 2A-2C illustrates various example port protective caps which may include various mechanisms for attachment.
Figure 2B:
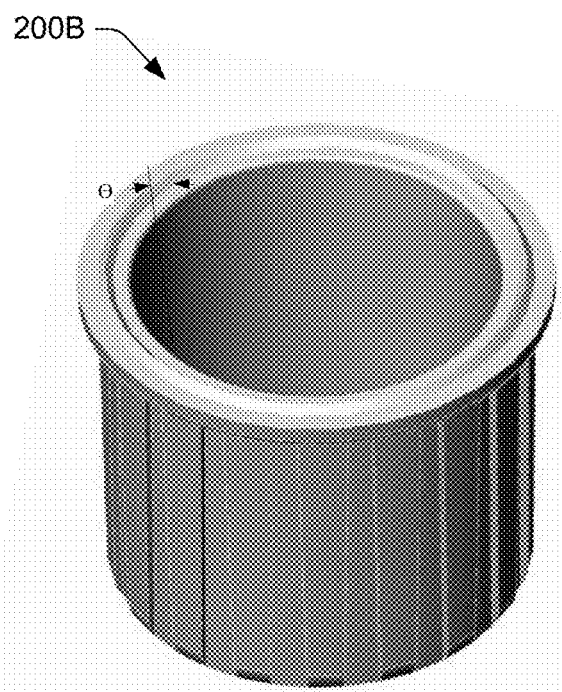
Figure 2C:
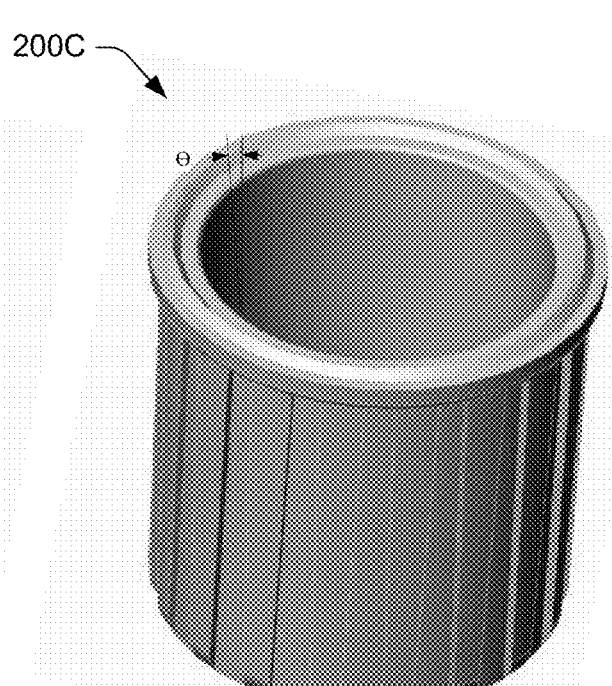

FIGS. 2A-2C illustrate several variations of IV port protective caps 200A, 200B, and 200C, respectively (collectively referred to as protective caps 200), for use with IV port connectors of varying outer diameter (OD), such as male Leur® connectors. The protective caps 200 of these embodiment are slip fit caps, in that they are designed to slip over and fit securely on IV port connectors of varying OD, since not all port connectors have standardize OD.

FIG. 2A illustrates a protective cap 200A having a stepped inner surface, including a first inner surface 202 and a second inner surface 204, the second inner surface 204 having a smaller average diameter than the first inner surface. The first and second inner surfaces 202 and 204 may have diameters chosen to match ODs of common ports on the market, of maximum and minimum ODs of ports on the market, or based on other criteria. Further both of the first and second inner surfaces 202 and 204 may be tapered (i.e., have a draft angle θ), such that a diameter of the first and second inner surfaces is largest closest to an opening of the protective cap 200A and decreases toward the bottom, closed end of the protective cap. A draft angle of the first inner surface 202 may be the same as, greater than, or less than a draft angle of the second inner surface 204. When the protective cap 200A is placed on an IV port, the protective cap 200A will slide over the IV port until an OD of the IV port contacts and seals against the interior surface of the protective cap 200A at either the first inner diameter 202 (in the case of an IV port with a relatively large OD) or the second inner diameter 204 (in the case of an IV port with a relatively small OD).

FIGS. 2B and 2C illustrate alternative embodiments of slip fit protective caps 200B and 200C, respectively, which have continuous, smooth inner surfaces. Rather than being stepped as in the embodiment of FIG. 2A, the protective caps 200B and 200C have continuous, smooth inner surfaces. Like the inner surfaces of the stepped protective cap 200, the inner surfaces of the protective caps 200B and 200C are tapered to accommodate IV ports of varying OD. However, in order to accommodate IV ports having a wide range of ODs, the draft angle θ of the protective caps needs to be larger (i.e., a more pronounced taper) as in the case of protective cap 200B, and/or the protective cap needs to be made deeper, as in the case of protective cap 200C.

Figure 3:
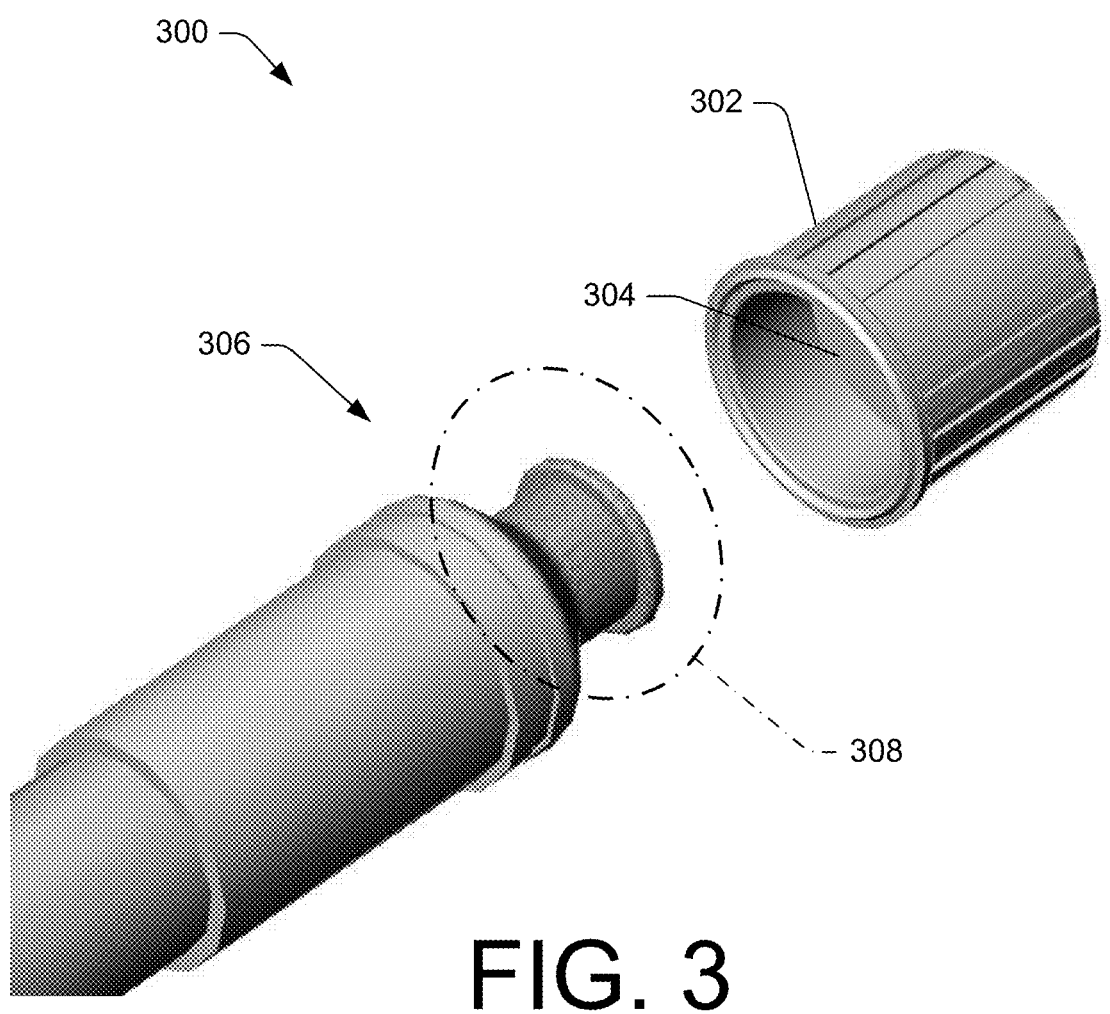
FIG. 3 illustrates an example port cleansing cap.

FIG. 3 illustrates an example IV port cleaning system 300 including a cleaning cap 302 having an applicator material 304 carrying an antimicrobial composition. The cleaning cap 302 may be used to clean an IV port 306. In the illustrated example, the IV port comprises a female Leur® connector. However, in other embodiments, such IV port cleaning systems may be used or adapted for use in cleaning male Leur® connectors, as well as other types of IV and non-IV ports and/or lumens. The cleaning cap 302 may be used to disinfect the IV port 306, for example, prior to connecting the port to a complimentary port, injecting a medication, drawing blood, or otherwise using the IV port 306. After being disinfected, volatile constituents of the antimicrobial composition may evaporate over time, leaving a film or barrier layer 308 of ethylenediaminetetraacetic acid (EDTA) or other chelating agent that may provide a lasting defense to contamination.

Once disinfected, a protective cap, such as one described above, may be applied to the IV port 306 to provide a physical barrier against recontamination. The protective cap may contain a same or different antimicrobial composition or other composition. In some implementations, the protective cap may securely couple to the IV port 306 and may seal the IV port. In the event that the antimicrobial composition in the protective cap dries out over time, the protective cap may still include a residual barrier layer of EDTA or other chelating agent that will provide further defense to contamination. In other embodiments, the protective cap may simply be coated with a film or barrier layer of EDTA or other chelating agent over all or part of the interior and/or exterior surfaces of the protective cap.

Figure 4A:
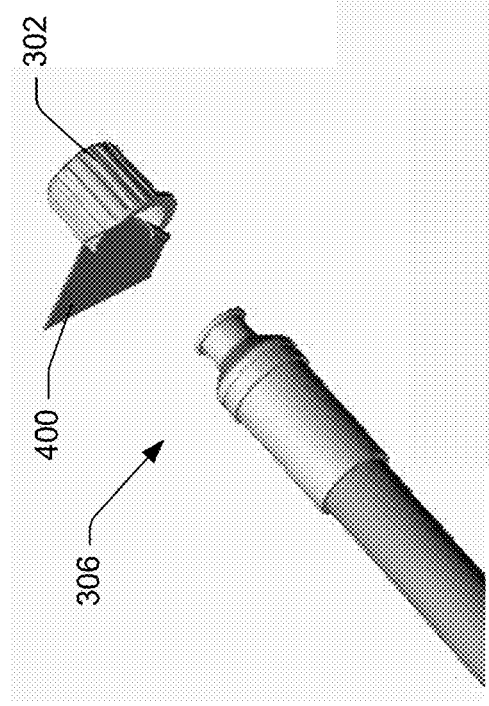
FIGS. 4A-4C illustrate an example port cleansing system.
Figure 4B:
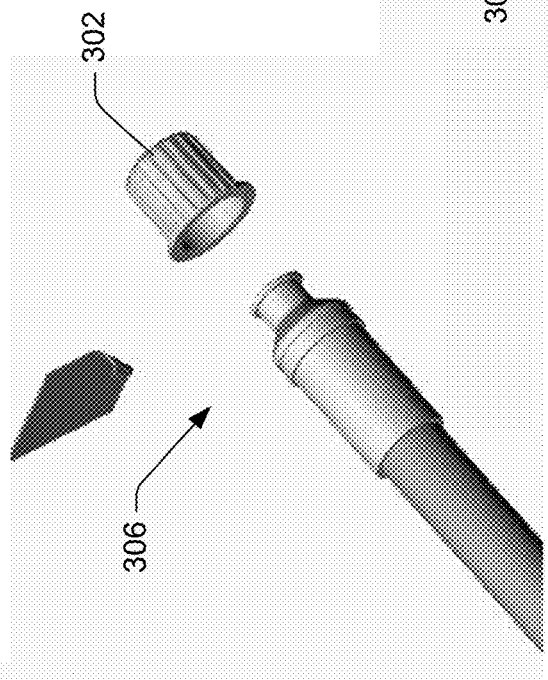
Figure 4C:
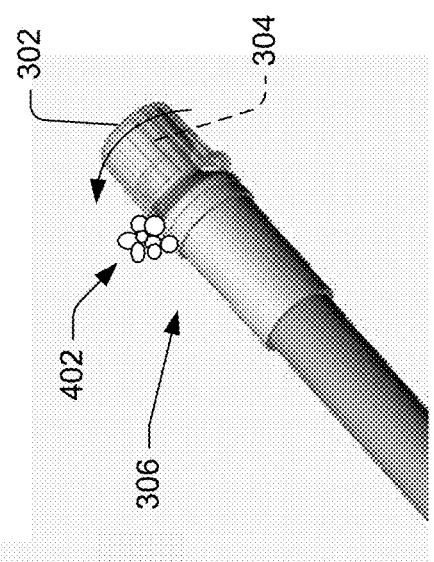

FIGS. 4A-4C illustrate the IV port cleaning and disinfection system 300 of FIG. 3 in more detail. Specifically, FIG. 4A illustrates the cleaning cap 302 prior to use. As shown in FIG. 4A, the cleaning cap 302 may come with a protective cover 400 that maintains the interior of the cleaning cap 302 in a sterile condition. Additionally or alternatively, the cleaning cap 302 may come packaged within another sterile package (not shown in this figure) to maintain the entire cleaning cap 302 in a sterile condition prior to use. In order to use the cleaning cap 302 to clean the IV port 306, the protective seal may be removed, exposing the interior of the cap 302, as shown in FIG. 4B. The cleaning cap 302 may then be placed onto the IV port 306 and twisted or otherwise used to scrub and clean the IV port 306. Specifically, the applicator material 304 carrying the antimicrobial composition may be used to scrub the exterior surfaces of the IV port 306 by twisting and pressing the cleaning cap 302 against the IV port 306.

If the IV port 306 is contaminated with bacteria, spores, parasites, viruses, bodily fluids, or other contaminants, the antimicrobial composition will begin to bubble or foam 402, providing a visual indicator of the contamination. The bubbling or foaming action is caused by reaction of the hydrogen peroxide with the bacteria, spores, parasites, and viruses. The hydrogen peroxide will also produce bubbles or foam in response to a Fenton reaction with the hemoglobin or platelets in the bodily fluids. The size and rate of bubble formation may be indicative of the level of contamination, giving the medical personnel a visual indication that the equipment is contaminated and may need further cleaning and/or replacement to avoid infection.

Figure 5A:
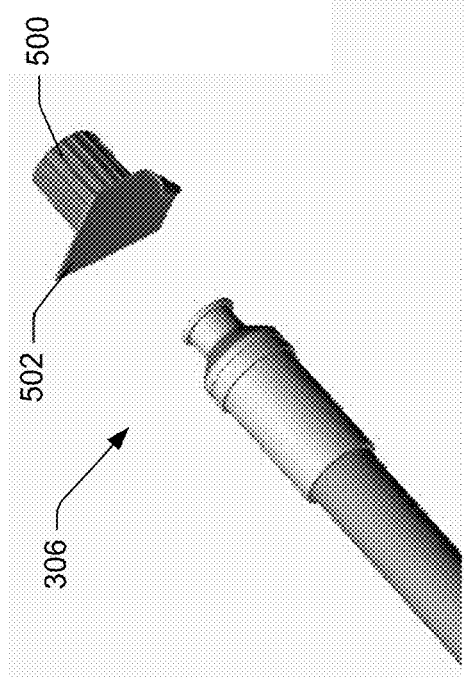
FIGS. 5A-5C illustrate example steps for attachment of an example port protective cap.
Figure 5B:
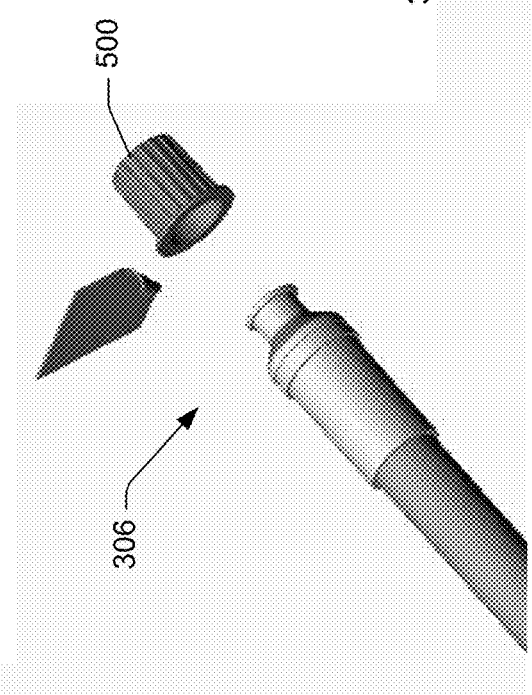
Figure 5C:
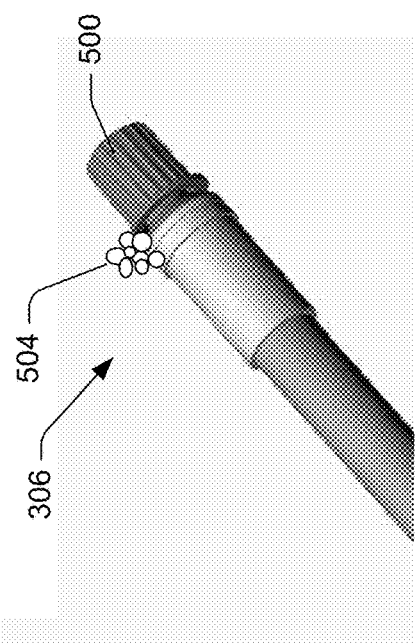

FIGS. 5A-5C illustrate an example protective cap 500 that may in some embodiments be used in combination with the cleaning cap 302 of FIG. 3 and FIGS. 4A-4C. After the IV port 306 has been cleaned, a protective cover 502 may be removed from the protective cap 500 to expose the interior of the protective cap, as shown collectively in FIGS. 5A and 5B. As with the cleaning cap 302, the protective cap 500 may come packaged within another sterile package (not shown in this figure) to maintain the entire protective cap 500 in a sterile condition prior to use.

The protective cap 500 may then be applied to the IV port 306 to provide a physical barrier against recontamination, as shown in FIG. 5C. The protective cap 500 may contain a same or different antimicrobial composition or other composition than the cleaning cap 302. If, when the protective cap 500 is coupled to the IV port 306, bubbling or foaming 504 occurs, this bubbling or foaming will provide a visual indicator to medical personnel that the IV port 306 is still contaminated and needs further cleaning and/or replacement.

In some embodiments, the antimicrobial composition in the cleaning cap 302 the protective cap 500, or both may include a dye or colorant that serves to further enhance the visual indication of contamination. When provided, the dye or colorant in the cleaning cap 302 may be the same or different color than that in the protective cap 500. For example, the dye or colorant may be of a color to match the color of the respective cap. In another example, the dye or colorant may be of a color to contrast with the color of the respective cap.

Additional details of example IV port cleaning and protective devices may be found in U.S. patent application Ser. No. 11/745,843, filed May 8, 2007, to Tennican, which is incorporated herein by reference.

Example Site Preparation Devices

Figure 6A:
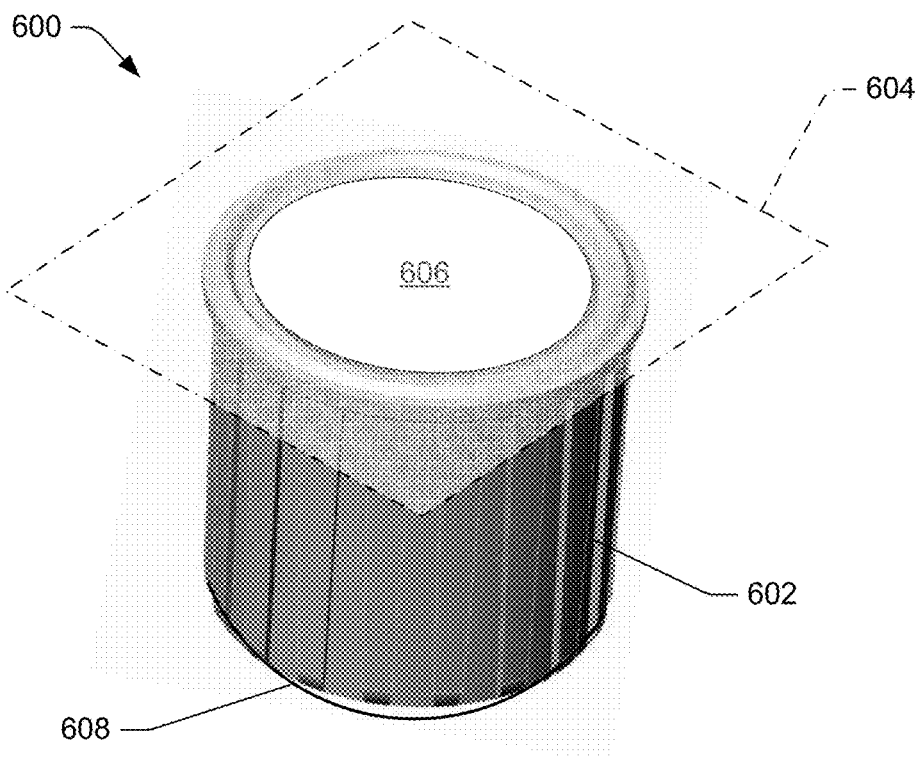
FIGS. 6A and 6B illustrate an example site cleaning and disinfecting device.
Figure 6B:
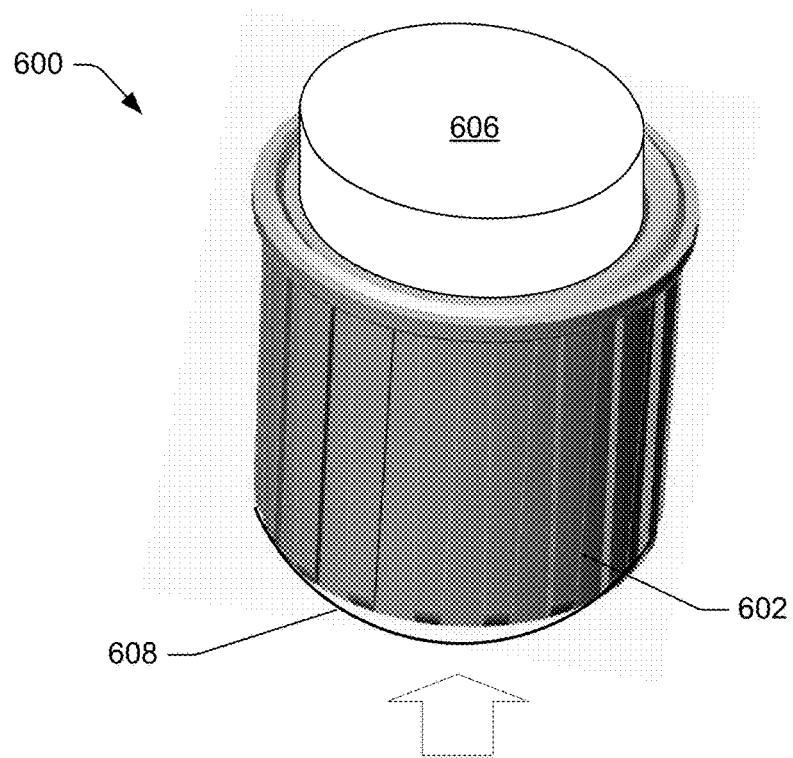

FIGS. 6A and 6B illustrate an example of a site cleaning and disinfecting device 600, which may be used to clean and/or disinfect intravascular (IV) line ports, other IV components (e.g., syringes, lumens, valves, etc.), injection sites, blood draw sites (e.g., from a vein, artery, or capillary), catheters and/or catheter insertion sites, wound sites, incision sites, peritoneal dialysis sites, a drainage sites, or any other site that is susceptible to infection.

The device 600 includes a housing or cap 602 sealed by a protective cover 604 (shown in broken lines in this figure to illustrate interior features of the device 600). Cap 602 may comprise and be constructed in similar form to protective caps 100 of FIGS. 1A and 1B. For example, cap 602 may be configured to include a "no-touch rim." Additionally, the protective cover 604 may be sealed to the cap 602 using the same techniques described above with respect to the protective cap 100 of FIGS. 1A and 1B. For example, and as described above, protective cover 604 may be fused with an energy director to aid in removal of protective cover. Housed within the cap 602 is an applicator material 608, such as a foam or sponge material, that holds an antimicrobial composition such as those described above. When the protective cover 604 is in place (as shown in FIG. 6A), the applicator material 606 is in a state of compression, such when the protective cover 604 is removed the applicator material 606 expands and protrudes from the interior cavity of the cap 602 (as shown in FIG. 6B) for use in cleaning or disinfecting the desired site.

In some embodiments, the cap 602 may include a flexible and/or domed bottom surface 608, which may be depressed (as shown by the arrow in FIG. 6B) to help to deploy the applicator material 606 from the interior cavity of the cap 602.

The applicator material 606 in this embodiment may comprise an open cell foam material, a foam material including open cell regions and closed cell regions, a sponge material, an abrasive material, a mesh material, or any other material suitable for cleaning or disinfecting a site. In some embodiments, the applicator material may comprise polyurethane, silicon, silicon rubber, polyethylene, polypropylene, thermoplastic elastomer, or the like and mixtures thereof. Also, while applicator material 606 is illustrated as being a generally cylindrical body, in other embodiments, the applicator material may take on other shapes and/or sizes. Further, the applicator material 606 may include different surface treatments (e.g., siping, slitting, etc.), surface finishes (e.g., macro-, micro-, or nano-structures, etc.), and/or contours (e.g., rounded, ribbed, protrusions, fingers, etc.).

Example Packaging of Cleaning Devices

Any of the various port and/or site cleaning devices described above may be packaged individually or in kits of multiple devices in a variety of packages.

Figure 7A:
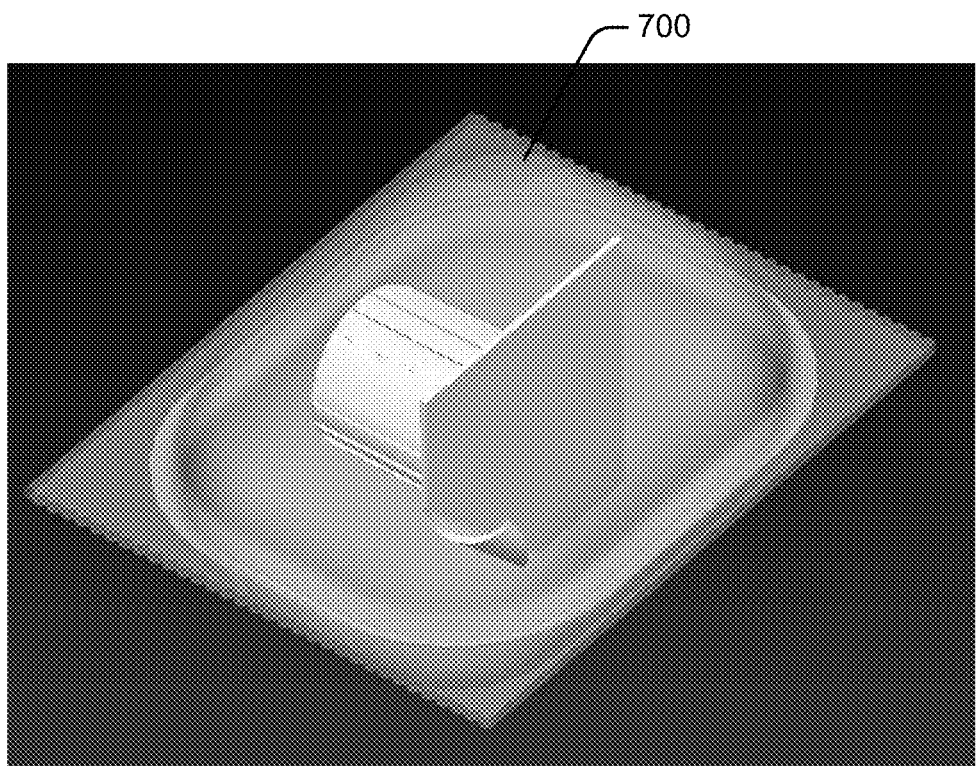
FIGS. 7A and 7B illustrate two example packing implementations of the port protective cap, port cleansing cap and/or the site cleaning and disinfecting device.
Figure 7B:
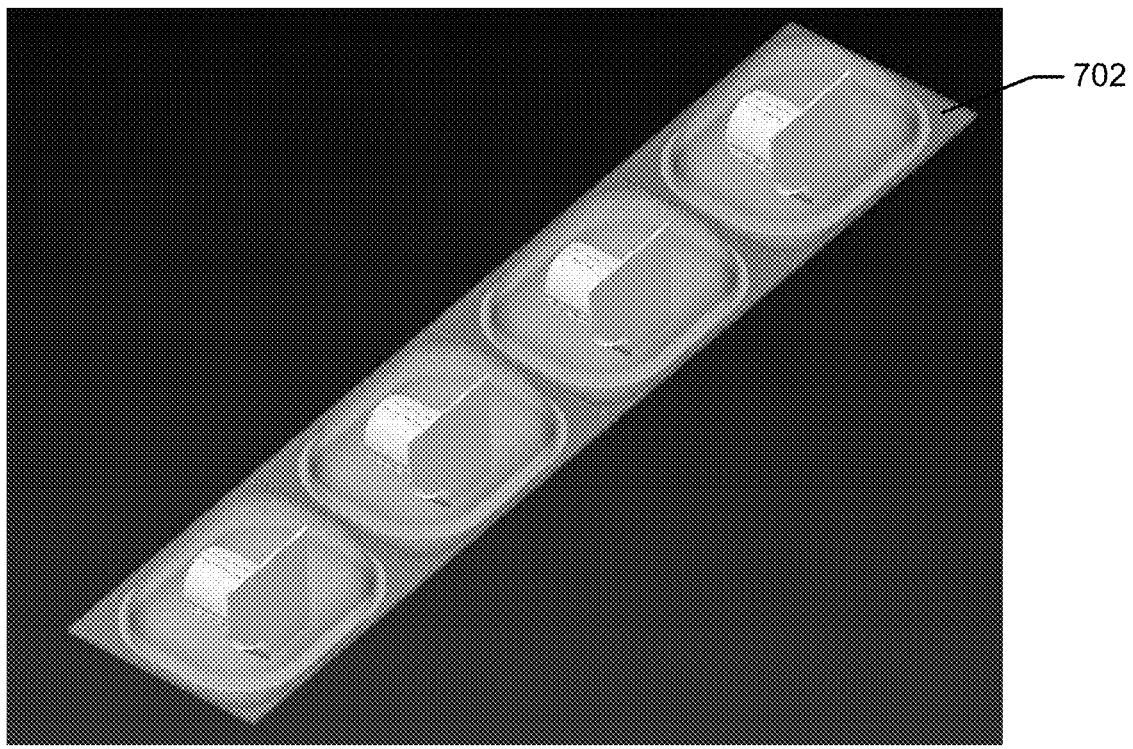

FIGS. 7A and 7B illustrate two example ways of packaging the port and/or site cleaning devices described herein. As shown in FIG. 7A, each device may be individually sealed in a pouch or packet 700 by sandwiching the device between multiple layers of thermoplastic material and sealing the sheets of material to each other around a periphery of the device by, for example, sonic welding, microwave welding, thermal bonding, or the like.

The approach described in FIG. 7A may be extended to simultaneously package multiple devices in a strip by placing multiple devices between sheets of thermoplastic material and then sealing the sheets of material to each other around the peripheries of each of the devices using any of the sealing methods described above. The result is a strip 702 containing multiple individually sealed devices. Individual devices may then by dispensed by cutting between the devices in the strip 702. Alternatively, the strip 702 may include perforations or score lines between the individual devices in the strip 702.

Figure 8A:
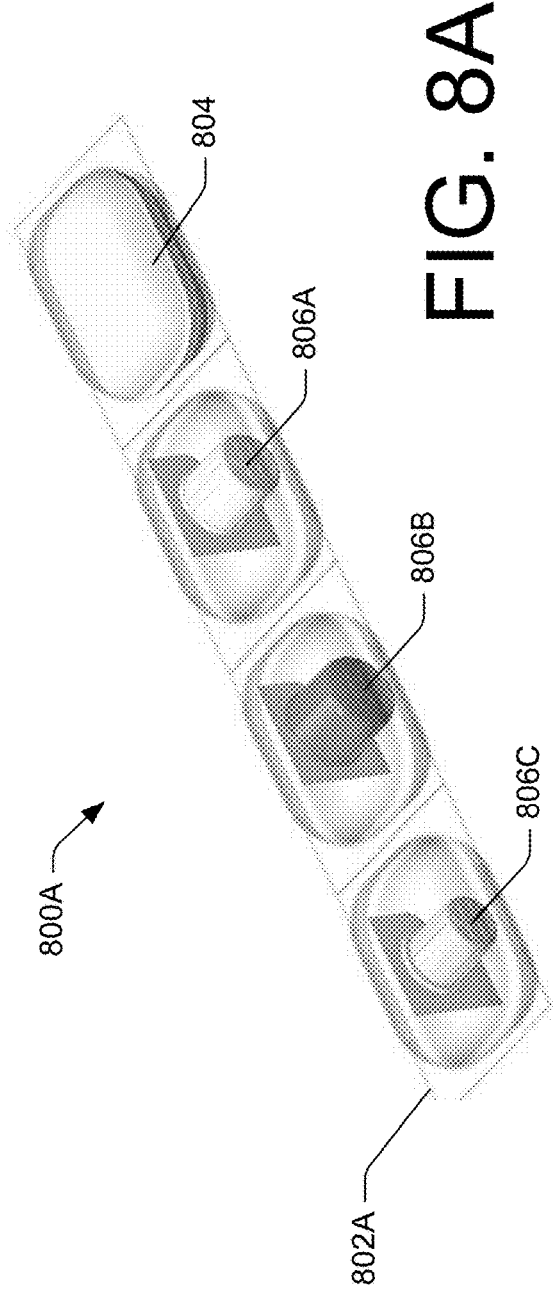
FIGS. 8A and 8B illustrate example strips or kits of the port protective caps, port cleansing caps and/or the site cleaning and disinfecting devices.
Figure 8B:
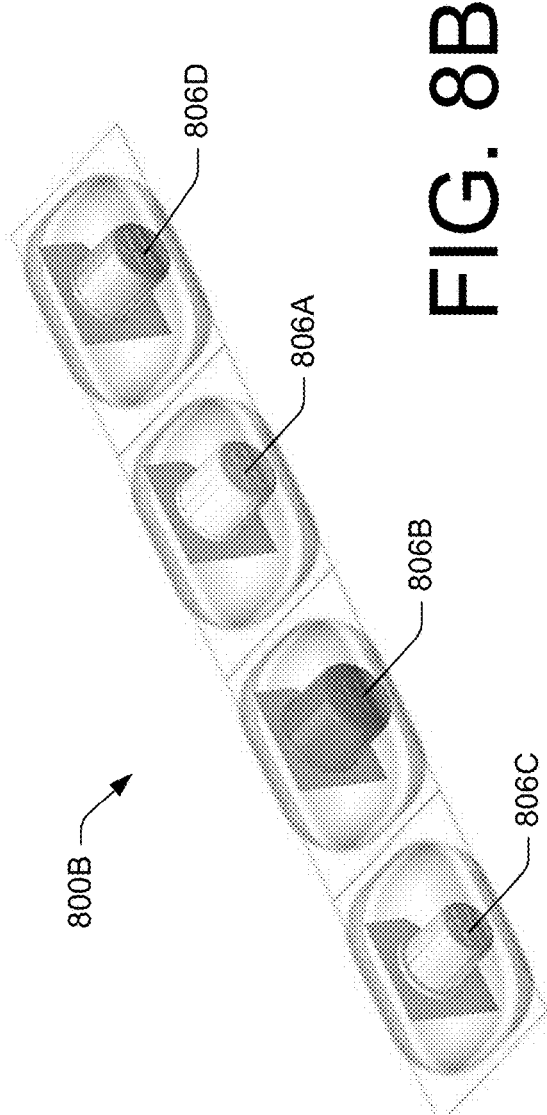

FIGS. 8A and 8B illustrate two example packages of port and/or site cleaning devices. As shown in FIG. 8A, a package 800A includes multiple different, individually packaged site cleaning devices, coupled together in a strip 802A or kit. The strip 802A may be packaged according to the methods described with reference to FIGS. 7A and 7B, or other methods. In the illustrated example, the package 800A includes a soap package 804, a first cap device 806A, a second cap device 806B, and a third cap device 806C (collectively referred to as cap devices 806). The soap pouch 804 may be used to provide an initial cleansing of the site and may comprise any known cleanser used in the medical industry. The different cap devices may comprise port cleaning caps, protective caps, site cleaning caps, or combinations of these. In some examples, the cap devices 806 may correspond to caps having different antimicrobial compositions and/or different concentrations of antimicrobial compositions.

In one specific example, the first cap device 806A (e.g., a yellow cap) may have a relatively high concentration of hydrogen peroxide, alcohol, and/or chelating agent, the second cap device 806B (e.g., a blue cap) may have lower concentration of hydrogen peroxide, alcohol, and/or chelating agent than the first cap device, and the third cap device 806C (e.g., a green cap) may have a lower concentration of hydrogen peroxide, alcohol, and/or chelating agent than the second cap device. In that case, the first cap device 806A may be used to clean the site first, followed by the second cap device 806B, and finally by the third cap device 806C. The higher concentrations of antimicrobial compositions may provide higher levels of disinfection, but may cause irritation to a patient's tissue especially if allowed to remain in contact with the tissue for a prolonged period. The approach described above may serve to provide high level disinfection using the first cap, followed by removal of the higher concentrations of antimicrobial composition by the second and third caps so as to minimize the risk of irritation of the patient's tissue.

FIG. 8B illustrates a package 800B, which is the same as package 800A, except that instead of the soap pouch 804, the package 800B includes a fourth cap device 806D. The fourth cap device 806D may include a soap composition similar to the soap pouch 804 or may include an antimicrobial composition having a concentration of hydrogen peroxide, alcohol, and/or chelating agent higher than that of the first cap 806A.

Example Antimicrobial Composition

In one example implementation, antimicrobial compositions that may be used in connection with the approaches described herein may include those described in, for example, U.S. patent application Ser. No. 12/874,188, filed Sep. 1, 2010, to Tennican et al., which is incorporated herein by reference. In that case, the antimicrobial compositions may include water ($H_2O$), a strong and non-toxic chelating agent such a EDTA (e.g., disodium EDTA, calcium disodium EDTA, magnesium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. However, in other examples, other antimicrobial compositions may be used in combination with the devices described in this application.

The antimicrobial compositions may be in a liquid form, a gel form, or a foam form, for example, and may be combined with one or more carriers or diluents, depending on the needs of a specific application. For example, in applications in which the antimicrobial composition is used as a hand sanitizer, the antimicrobial composition may be in a gel form. As another example, if the antimicrobial composition is used as a cleaning agent, a flush solution, or an irritant, the antimicrobial composition may be in a liquid form. In that case, the concentration of the various constituents may depend on, for example, a desired level of disinfection, whether the composition is being applied directly to living tissue or to a medical device, and/or to avoid irritation of tissue to which the composition will be applied directly or indirectly (e.g., via a medical device to which the composition is or was applied). In another example, a liquid form of the antimicrobial compositions may be vaporized or sprayed for application to nasal passages or other airways of a patient. In yet another example, the antimicrobial compositions may include or be combined with a lubricant (e.g., glycerin), surfactant or emulsifier (e.g., glycerol monolaurate (GML)), or the like and may be applied to a catheter, tracheal tube, scope, instrument, or other device that is to be inserted into a patient's body.

CONCLUSION

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A method of preventing the spread of infectious agents comprising:
    identifying a surface to be sanitized or disinfected; and
    applying a medical applicator to the surface to thereby sanitize or disinfect the surface, the medical applicator comprising:
        a cap having a threaded inner surface with a cylindrical cavity, a base, and a flange at an opening of the cylindrical cavity to affix a protective cover;
        an applicator material compressed in an area defined by the cylindrical cavity and the base of the cylindrical cavity of the cap by the affixation of the protective cover, the applicator material having an insert bottom in contact with the inner surface of the base and being larger than the area when uncompressed and extending beyond the opening of the cylindrical cavity when the protective cover is removed; and
        an antimicrobial or antiseptic agent disposed within the applicator material.

2. The method of claim 1, wherein the surface to be sanitized or disinfected is an area of human tissue or an area on a medical device.

3. The method of claim 1, wherein the applicator material is a foam insert.

4. The method of claim 3, wherein the foam insert is a cylindrical or rectangular shape.

5. The method of claim 3, wherein the foam insert comprises an open-cell foam insert.

6. The method of claim 4, wherein the foam insert comprises an inner open-cell layer connecting two outer closed-cell layers at a top and a bottom of the cylindrical or rectangular shape.

7. The method of claim 1, wherein the applicator material is a sponge.

8. The method of claim 1, wherein the opening of the cylindrical cavity includes a rim traveling a circumference of the opening of the cylindrical cavity and wherein the flange is disposed on the rim as a raised ridge having a smaller cross-sectional width as compared to the rim and the flange configured to extend distally from the rim to fuse with the removable protective cover.

9. The method of claim 1, wherein the antimicrobial or antiseptic agent comprises one or more of a surfactant, water, a low molecular weight alcohol, a peroxide, a peroxide generating agent or a chelating agent.

10. The method of claim 1, wherein the cap further comprises the protective cover removably affixed to the flange and compressing the applicator material into the area defined by the cylindrical cavity of the cap and the protective cover.

11. A medical device comprising:
    a cap having a threaded inner surface with a cylindrical cavity, a base, and a flange at an opening of the cylindrical cavity to affix a protective cover; and
    an applicator material compressed in an area defined by the cylindrical cavity and the base of the cylindrical cavity of the cap by the affixation of the protective cover, the applicator material having an insert bottom in contact with the inner surface of the base and being larger than the area when uncompressed and extending beyond the opening of the cylindrical cavity when the protective cover is removed.

12. The medical device of claim 11, wherein the applicator material is a foam insert.

13. The medical device of claim 12, wherein the foam insert is a cylindrical or rectangular shape.

14. The medical device of claim 12, wherein the foam insert comprises an open-cell foam insert.

15. The medical device of claim 13, wherein the foam insert comprises an inner open-cell layer connecting two outer closed-cell layers at a top and a bottom of the cylindrical or rectangular shape.

16. The medical device of claim 11, wherein the applicator material is a sponge.

17. The medical device of claim 11, wherein the applicator material includes an antimicrobial composition comprising one or more of a surfactant, water, a low molecular weight alcohol, a peroxide, a peroxide generating agent or a chelating agent.

18. The medical device of claim 11, wherein the opening of the cylindrical cavity includes a rim traveling a circumference of the opening of the cylindrical cavity and wherein the flange is disposed on the rim as a raised ridge having a smaller cross sectional width as compared to the rim and the flange configured to extend distally from the rim to fuse with the removable protective cover.

19. The medical device of claim 11, further comprising a package for storing the cap, the package configured to store one or more caps separate from one another.

20. The medical device of claim 11, further comprising the protective cover removably affixed to the flange and compressing the applicator material into the area defined by the cylindrical cavity of the cap and the protective cover.

* * * * *